United States Patent
Behnke, II et al.

(10) Patent No.: US 9,192,425 B2
(45) Date of Patent: Nov. 24, 2015

(54) SYSTEM AND METHOD FOR TESTING ELECTROSURGICAL GENERATORS

(71) Applicant: COVIDIEN LP, Mansfield, MA (US)

(72) Inventors: Robert J. Behnke, II, Erie, CO (US); Peter L. Valentyik, Boulder, CO (US); Scott E. M. Frushour, Boulder, CO (US)

(73) Assignee: Covidien LP, Mansfield, MA (US)

( * ) Notice: Subject to any disclaimer, the term of this patent is extended or adjusted under 35 U.S.C. 154(b) by 120 days.

(21) Appl. No.: 13/889,517

(22) Filed: May 8, 2013

(65) Prior Publication Data

US 2013/0345696 A1    Dec. 26, 2013

Related U.S. Application Data

(60) Provisional application No. 61/664,547, filed on Jun. 26, 2012.

(51) Int. Cl.
*A61B 18/10* (2006.01)
*A61B 18/04* (2006.01)
(Continued)

(52) U.S. Cl.
CPC ......... *A61B 18/1233* (2013.01); *A61B 18/1206* (2013.01); *A61B 18/1815* (2013.01);
(Continued)

(58) Field of Classification Search
CPC .............. A61B 18/12; A61B 18/1233; A61B 2018/00988; A61B 2018/00636; A61B 2017/00707; A61B 2017/00712; A61B 2017/00716; A61B 2017/00734; A61B 2017/00725
USPC .......................................... 606/34
See application file for complete search history.

(56) References Cited

U.S. PATENT DOCUMENTS 3,727,139 A * 4/1973 Gallant et al. ............. 455/196.1
5,300,068 A * 4/1994 Rosar et al. ...................... 606/34
(Continued)

FOREIGN PATENT DOCUMENTS

DE       179607       3/1905
DE      1099658       2/1961
(Continued)

OTHER PUBLICATIONS

D W Knight, http://www.g3ynh.info/zdocs/z_matcing/part_2.html, 2007-2009, accessed Oct. 21, 2014.*
(Continued)

*Primary Examiner* — Ronald Hupczey, Jr.
*Assistant Examiner* — Bo Ouyang (57) ABSTRACT

A system is provided. The system includes an electrosurgical generator configured to measure, collect and record data pertaining to a characteristic of tissue as the tissue is being electrosurgically treated. A tuner configured to couple to the electrosurgical generator includes a tuning circuit providing a load having a variable complex impedance for the electrosurgical generator when the electrosurgical generator is connected thereto. A controller including stored data pertaining to impedance values is in operable communication with the electrosurgical generator for retrieving the recorded data pertaining to the characteristic of tissue. The controller is in operable communication with the tuner for varying a complex impedance of the load. The controller configured to compare the recorded data pertaining to the at least one characteristic of tissue with the stored data pertaining to the plurality of impedance values and to adjust the tuner to one of the plurality of impedance values.

21 Claims, 4 Drawing Sheets

(51) Int. Cl.
*A61B 18/12* (2006.01)
*A61B 18/18* (2006.01)
*A61B 17/00* (2006.01)
*A61B 18/00* (2006.01)

(52) U.S. Cl.
CPC ............. *A61B2017/00707* (2013.01); *A61B 2017/00725* (2013.01); *A61B 2018/0063* (2013.01); *A61B 2018/00684* (2013.01); *A61B 2018/00755* (2013.01); *A61B 2018/00869* (2013.01); *A61B 2018/00875* (2013.01); *A61B 2018/00988* (2013.01); *A61B 2018/1823* (2013.01)

(56) References Cited

U.S. PATENT DOCUMENTS

| | | | |
|---|---|---|---|
| 5,957,969 A * | 9/1999 | Warner et al. | 607/156 |
| D574,323 S | 8/2008 | Waaler | |
| 8,212,629 B1 * | 7/2012 | Tsironis | 333/17.3 |
| 2010/0121318 A1 | 5/2010 | Hancock | |
| 2012/0239026 A1 | 9/2012 | Orszulak | |
| 2013/0035679 A1 | 2/2013 | Orszulak | |
| 2013/0053840 A1 | 2/2013 | Krapohl | |
| 2013/0066311 A1 | 3/2013 | Smith | |
| 2013/0067725 A1 | 3/2013 | Behnke, II | |
| 2013/0072920 A1 | 3/2013 | Behnke, II | |
| 2013/0072921 A1 | 3/2013 | Behnke, II | |
| 2013/0072922 A1 | 3/2013 | Behnke, II | |
| 2013/0072923 A1 | 3/2013 | Behnke, II | |
| 2013/0079763 A1 | 3/2013 | Heckel | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

Larry Benko, www.w0qe.com/Papers/Antenna_Tuners.pdf, Jun. 1, 2011, accessed Oct. 21, 2014 (pp. 31-32).*
Extended European Search Report corresponding EP 13 17 3776.9, completed Nov. 7, 2013 and mailed Nov. 18, 2013; (6 pp).
"Electrosurgical Unit Analyzer ESU-2400 Series User Manual"; www.bcgroupintl.com; Apr. 1, 2012; pp. 6, 11, 73.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/485,083, filed May 31, 2012, Robert J. Behnke, II.
U.S. Appl. No. 13/587,400, filed Aug. 16, 2012, James H. Orszulak.
U.S. Appl. No. 13/652,932, filed Oct. 16, 2012, Wham.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance" Applied Neurophysiology 51: (1988) pp. 230-242.

Zlatanovic M., "Sensors in Diffusion Plasma Processing" Microelectronics 1995; Proceedings 1995; 20$^{th}$ International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

\* cited by examiner

SYSTEM AND METHOD FOR TESTING ELECTROSURGICAL GENERATORS

CROSS REFERENCE TO RELATED APPLICATION

The present application claims the benefit of and priority to U.S. Provisional Application Ser. No. 61/664,547, filed on Jun. 26, 2012, the entire contents of which are incorporated herein by reference.

BACKGROUND

1. Technical Field

The present disclosure relates to systems and methods for testing electrosurgical generators. More particularly, the present disclosure relates to systems and methods including a controller, tuner and step motor configured to simulate an electrosurgical procedure for testing electrosurgical generators to support a variety of developmental and research activities associated therewith.

2. Description of Related Art

Electrosurgical generators that are utilized in conjunction with one or more types of electrosurgical instruments to electrosurgically treat tissue are well known in the art. For example, and in one particular instance, the electrosurgical generator and instrument may be configured to seal tissue. As is known in the art, sealing tissue, typically, includes (in the broadest sense) the steps of grasping tissue with jaw members associated with the electrosurgical instrument and providing electrosurgical energy to the grasped tissue to seal the tissue. To create an effective tissue seal, a specific gap distance (e.g., in the range from about 0.001 inches to about 0.006) needs to be maintained between the jaw members during the sealing process. In addition, a specific pressure (e.g., in the range from about 3 $kg/cm^2$ to about 16 $kg/cm^2$) needs to be maintained on tissue during the sealing process. Moreover, one or more controllers are associated with the electrosurgical generator and are configured to control the amount of electrosurgical energy that is provided to the jaw members during the sealing cycle. All of these three factors contribute in providing an effective, uniform and consistent tissue seal. In certain instances, after the tissue is sealed, one or more suitable devices may be utilized to sever the sealed tissue.

During the sealing process, characteristics of tissue, e.g., impedance of tissue, change due to the fact that the tissue is being heated, desiccated fused and dehydrated. In particular, goes through this cycle, the tissue impedance characteristics change which, in turn, cause the real and imaginary parts of the impedance to behave differently. Most electrosurgical generators are equipped to handle these changes in impedance such that tissue can be effectively sealed. In particular, one or more control algorithms, sensors, etc., in operable communication with the electrosurgical generator are, typically, configured to monitor and compensate for these changes in impedance during the sealing cycles.

Electrosurgical generators may be tested prior to use to ensure that the electrosurgical generator and operable components associated therewith will function as intended during an electrosurgical procedure. As is conventional in the art, to test the electrosurgical generators, a sealing phase may be simulated utilizing a range of resistors with fixed values that are placed on an output of the electrosurgical generator. The fixed resistors are configured to represent tissue that is to be sealed. With the resistors in place at the output of the electrosurgical energy, the electrosurgical generator may be run through a simulated sealing cycle and relevant data pertaining to the sealing simulation may be collected. As can be appreciated, this testing method only provides data that pertains to "purely" resistive loads. As noted above, however, tissue impedance includes both real and imaginary parts, which behave differently. Accordingly, the aforementioned testing method may not provide an accurate or complete representation of the changes in tissue impedance as the tissue is being sealed.

SUMMARY

In view of the foregoing, systems and methods including a controller, tuner and step motor configured to simulate an electrosurgical procedure for testing electrosurgical generators to support a variety of development activities associated therewith may prove useful in the medical field.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a system. The system includes an external measurement device that is configured to measure, collect and record data pertaining to at least one characteristic of tissue as the tissue is being electrosurgically treated. A tuner is configured to couple to an electrosurgical generator and includes at least one tuning circuit that is configured to provide a load having a variable complex impedance for the electrosurgical generator when the electrosurgical generator is coupled to the tuner. A controller is configured to couple to the electrosurgical generator for diagnostic testing thereof. The controller includes stored data pertaining to a plurality of impedance values. The controller is in operable communication with the external measurement device for retrieving the recorded data pertaining to the at least one characteristic of tissue and in operable communication with the tuner for varying a complex impedance of the load. The controller is configured to compare the recorded data pertaining to the at least one characteristic of tissue with the stored data pertaining to the plurality of impedance values and to adjust the tuner to at least one of the plurality of impedance values during diagnostic testing of the electrosurgical generator.

A step motor may be configured to operably couple to the controller and tuner. In this instance, the controller may be configured to activate the step motor for varying the complex impedance of the load.

An impedance analyzer may be configured to operably couple to the controller and tuner when the controller and tuner are not coupled to the electrosurgical generator or the external measurement device. In this instance, the impedance analyzer may be configured to measure the complex impedance of the load as the step motor varies the complex impedance of the load. Moreover, the measured complex impedances of the load may be stored in the controller as the data pertaining to the plurality of impedance values.

The tuner may be, but is not limited to a passive tuner, a high frequency tuner, a microwave tuner, a solid state tuner and an active tuner. In the particular instance where the tuner is a passive tuner, it includes a variable Pi network having a first variable capacitor connected in parallel with one or more variable inductors that is connected in parallel with a second variable capacitor that is connected in parallel with one or more resistors. Each of the first and second variable capacitors may include a capacitance that can vary from about 40 pF to about 2,000 pF and the inductor(s) may include an inductance that can vary from about 50 uH to about 200 uH.

An aspect of the present disclosure provides a method for testing electrosurgical generators. An external measurement device configured to measure, collect and record data pertaining to at least one characteristic of tissue as the tissue is being electrosurgically treated is provided. An electrosurgical generator is coupled to a tuner including at least one tuning circuit configured to provide a load having a variable complex impedance for the electrosurgical generator when the electrosurgical generator is coupled to the tuner. The external measurement device is coupled to a controller for retrieving the recorded data pertaining to the at least one characteristic of tissue. The controller is coupled to the electrosurgical generator to perform a diagnostic test thereof. The controller includes stored data pertaining to a plurality of impedance values. The controller is coupled to the tuner for varying a complex impedance of the load. The recorded data pertaining to the at least one characteristic of tissue is compared with the stored data pertaining to the plurality of impedance values. The tuner is adjusted to at least one of the plurality of impedance values during diagnostic testing of the electrosurgical generator.

The method may include providing the external measurement device as a component of the electrosurgical generator.

A step motor may be provided and configured to operably couple to the controller and tuner. In this instance, the step motor may be activated for varying the complex impedance of the load.

An impedance analyzer may be provided and configured to operably couple to the controller and tuner when the controller and tuner are not coupled to the electrosurgical generator or the external measurement device. In this instance, the complex impedance of the load may be measured with the impedance analyzer as the step motor varies the complex impedance of the load.

The measured complex impedances of the load may be stored in the controller as the data pertaining to the plurality of impedance values. In addition, step positions of the step motor may be stored in the controller. The step positions correspond to the measured complex impedances of the load.

The tuner may be, but is not limited to a passive tuner, a high frequency tuner, a microwave tuner, a solid state tuner and an active tuner. In the particular instance where the tuner is a passive tuner, it includes a variable Pi network having a first variable capacitor connected in parallel with one or more variable inductors that is connected in parallel with a second variable capacitor that is connected in parallel with one or more resistors. Each of the first and second variable capacitors may include a capacitance that can vary from about 40 pF to about 2,000 pF and the inductor(s) may include an inductance that can vary from about 50 uH to about 200 uH.

An aspect of the present disclosure provides a system for testing electrosurgical generators. The system includes an electrosurgical generator that is configured to provide electrosurgical energy for electrosurgically treating tissue and to measure, collect and record data pertaining to at least one characteristic of tissue as the tissue is being electrosurgically treated. A tuner is configured to couple to the electrosurgical generator and includes at least one tuning circuit including a load including at least three reactive components and at least one resistor. The tuning circuit provides a load having variable complex impedance for the electrosurgical generator when the electrosurgical generator is coupled to the tuner. A controller includes stored data pertaining to a plurality of impedance values. The controller is configured to couple to the electrosurgical generator for diagnostic testing thereof and for retrieving the recorded data pertaining to the at least one characteristic of tissue. The controller is configured to couple to a step motor that is configured to couple to the tuner for varying at least one of the at least three reactive components to vary a complex impedance of the load of the tuner. The controller is configured to compare the recorded data pertaining to the at least one characteristic of tissue with the stored data pertaining to the plurality of impedance values and to adjust the tuner to at least one of the plurality of impedance values.

An impedance analyzer may be configured to operably couple to the controller and tuner when the controller and tuner are not coupled to the electrosurgical generator. In this instance, the impedance analyzer may be configured to measure the complex impedance of the load as the step motor varies the complex impedance of the load. The measured complex impedances of the load may be stored in the controller as the data pertaining to the plurality of impedance values.

The reactive components may include a first variable capacitor connected in parallel with one or more variable inductors that are connected in parallel with a second variable capacitor that is connected in parallel with one or more resistors. Each of the first and second variable capacitors may include a capacitance that can vary from about 40 pF to about 2,000 pF and the inductor(s) may include an inductance that can vary from about 50 uH to about 200 uH.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

A system in accordance with the instant disclosure can be used to support a variety of developmental and research activities of an electrosurgical generator. The system utilizes voltage, current and phase parameters obtained at a surgical site during an electrosurgical procedure. These parameters can be reproduced and simulated during bench top testing to support, without limit to, algorithm development, design verification, software validation, reliability and manufacturing testing of electrosurgical generators. In addition, efficiency gains associated with electrosurgical generators can also be realized through automated testing using the system of the instant disclosure.

Figure 1:
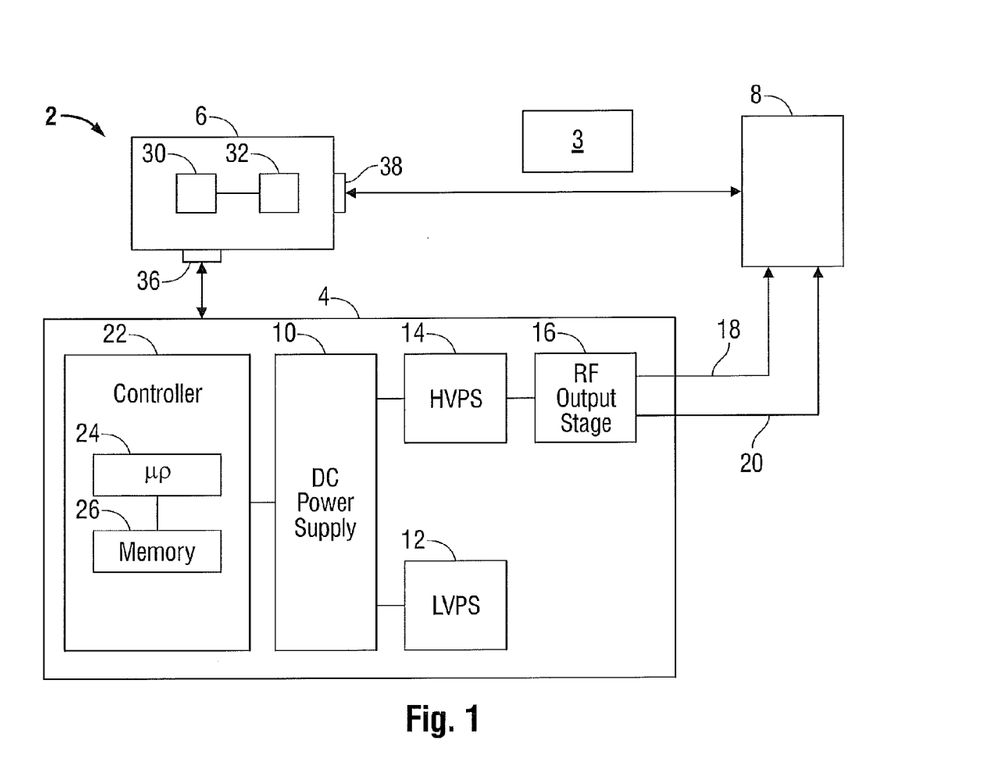
FIG. 1 is a schematic block diagram of a system utilized for testing electrosurgical generators according to an embodiment of the instant disclosure.

With reference to FIG. 1, a system 2 for testing electrosurgical generators is illustrated. System 2 includes an external measurement device 3, a controller 6 and one or more tuners 8.

In accordance with the instant disclosure, the external measurement device 3 may be any suitable measurement device known in the art. As used herein, the measurement device 3 is configured to measure, collect, calculate and record one or more electrical parameters at a surgical site to determine an impedance of tissue as the tissue is being electrosurgically treated. Suitable measurement devices 3 may include without limitation spectrum analyzers, oscilloscopes, and the like. For the purposes herein, however, it is assumed that a generator 4 includes a measurement device 3 therein that is configured to measure, collect, calculate and record one or more electrical parameters at a surgical site to determine an impedance of tissue as the tissue is being electrosurgically treated (FIG. 1). Alternatively, the measurement device 3 may be configured to selectively couple to the generator 4.

Continuing with reference to FIG. 1, generator 4 includes suitable input controls (e.g., buttons, activators, switches, touch screen, etc.) for controlling the generator 4. The controls allow a user to adjust power of the RF energy, waveform parameters (e.g., crest factor, duty cycle, etc.), and other parameters to achieve the desired waveform suitable for a particular task (e.g., coagulating, tissue sealing, intensity setting, etc.).

Generator 4 includes a DC power supply 10 that is connected to a conventional AC source (e.g., electrical wall outlet) and includes a low voltage power supply 12 ("LVPS") and a high voltage power supply 14 ("HVPS") (FIG. 1). The HVPS 14 provides high voltage DC power to an RF output stage 16, e.g., an RF amp module, which then converts high voltage DC power into RF energy and delivers the RF energy to the active terminal 18. The energy is returned thereto via the return terminal 20. The LVPS 12 provides power to various components of the generator 4 (e.g., measurement device 3, input controls, displays, etc.). The generator 4 may include a plurality of connectors to accommodate various types of devices (e.g., an electrosurgical instrument, controller, tuner, external measurement device 3, etc.).

Generator 4 further includes a microcontroller 22 including a microprocessor 24 operably connected to a memory 26, which may be volatile type memory (e.g., RAM) and/or non-volatile type memory (e.g., flash media, disk media, etc.) (FIG. 1). The microcontroller 22 includes an output port that is operably connected to the DC power supply 10 and/or RF output stage 16 allowing the microprocessor 24 to control the output of the generator 4 according to either open and/or closed control loop schemes. Those skilled in the art will appreciate that the microprocessor 24 may be substituted by any logic processor (e.g., control circuit) adapted to perform the calculations discussed herein.

Generator 4 may be in operable communication with one or more sensors (not shown) that are configured to provide characteristic information pertaining to tissue as the tissue is being electrosurgically treated. The characteristic information pertaining to tissue may be communicated to the microcontroller 22 for processing by the microprocessor 24 and subsequent storage into memory 26.

Figure 8:
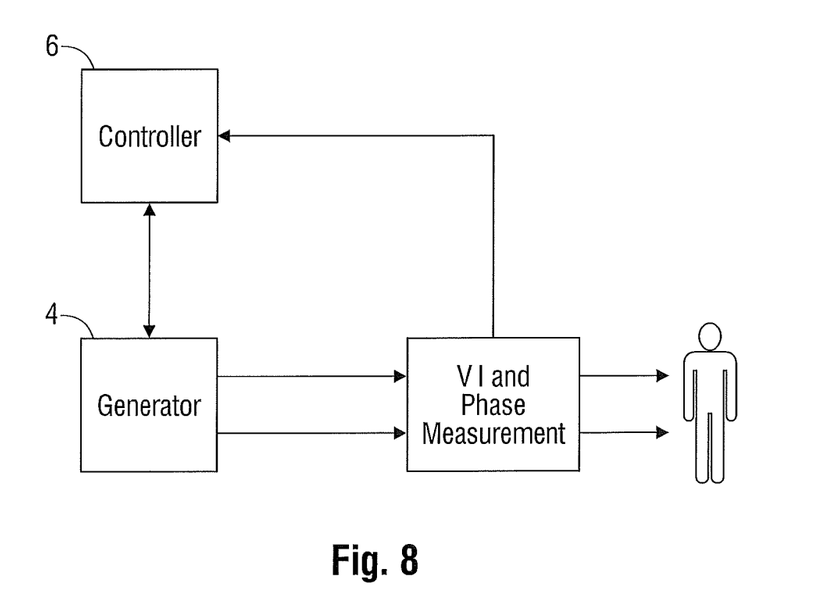
FIG. 8 is schematic block diagram of a sub-system of the system depicted in FIG. 1 utilized for recording tissue during an electrosurgical procedure.

In accordance with the instant disclosure, the generator 4 is configured to provide electrosurgical energy for electrosurgically treating tissue, see FIG. 8 for example. As noted above, generator 4 is also configured to measure, collect and record data pertaining to one or more characteristics of tissue, e.g., impedance of tissue, as the tissue is being electrosurgically treated. One or more electrical parameters, e.g., voltage, current, power, phase, etc. may be taken at the tissue site to calculate the impedance of tissue. This data pertaining to the impedance of tissue is stored in memory 26 and is accessible by controller 6 for future use thereof. In particular, the calculated tissue impedances are mapped to a Smith Chart by suitable methods and utilized by the controller 6 to manipulate the tuner 8 to match the calculated tissue impedances and vary an impedance of a load "L" of the tuner 8 with respect to time (as is described in greater detail below). As can be appreciated, this mapping to the Smith Chart can be done for a particular electrosurgical instrument utilized with the generator 4, electrosurgical procedure, tissue type, etc.

With continued reference to FIG. 1, controller 6 includes one or more microprocessors 30 operably connected to a memory 32, which may be volatile type memory (e.g., RAM) and/or non-volatile type memory (e.g., flash media, disk media, etc.). Those skilled in the art will appreciate that the microprocessor 30 may be substituted by any logic processor (e.g., control circuit) adapted to perform the calculations discussed herein. The controller 6 includes input and output ports 36 and 38, respectively, which allow the controller 6 to communicate with one or more components, e.g., generator 4, tuner 8, step motor 50, impedance analyzer 52, etc., of the system 2 (FIG. 1).

Controller 6 includes stored data that pertains to a plurality of impedance values. The plurality of impedance values are obtained by mapping passive components of the tuner 8 to a Smith Chart. Tuner 8 may be any suitable type of tuner including but not limited to those described in FIGS. 2-6.

Figure 2:
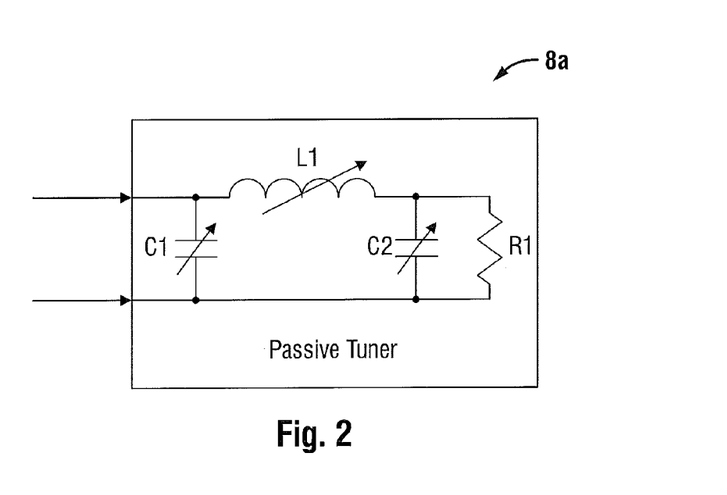
FIG. 2 is a schematic view of a passive tuner configured for use with the system depicted in FIG. 1.

FIG. 2 illustrates an RF tuner, e.g., a passive tuner 8a. The passive tuner 8a includes a variable Pi network having a first variable capacitor C1 connected in parallel with one or more variable inductors L1 that is connected in parallel with a second variable capacitor C2 that is connected in parallel with one or more resistors R1. Each of the first and second variable capacitors C1 and C2 include a capacitance that can vary from about 40 pF to about 2,000 pF and the inductor(s) may include an inductance that can vary from about 50 uH to about 200 uH. An advantage of a Pi network is that it covers an entire range of the Smith Chart with a minimal amount of passive components.

Figure 3:
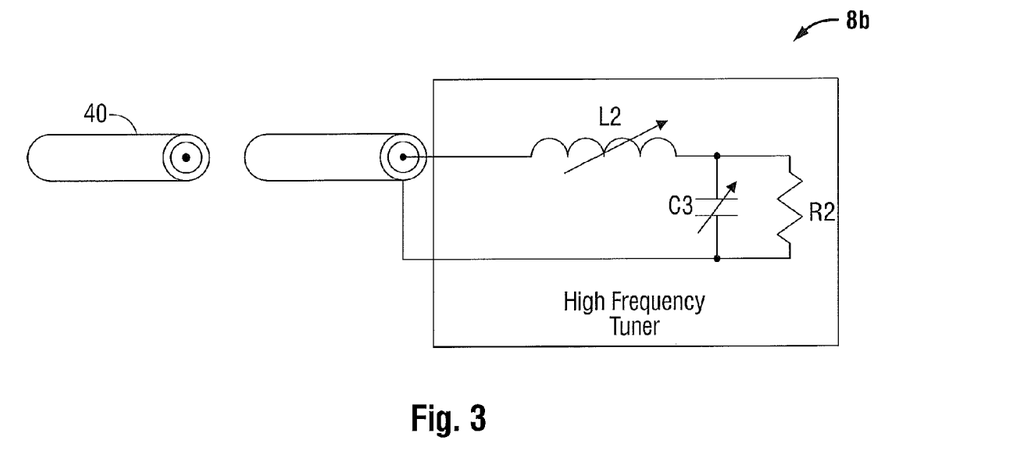
FIG. 3 is a schematic view of a high frequency tuner configured for use with the system depicted in FIG. 1.

FIG. 3 illustrates a high frequency tuner 8b. Unlike the passive tuner 8a, however, high frequency tuner 8b does not cover the entire range of the Smith Chart. This type of tuner is suitable for testing the generator 4 when the generator 4 is configured to transmit electrosurgical energy in the high frequency range, e.g., Megahertz frequency range. One advantage of the high frequency tuner 8b is that it utilizes only three passive components, a capacitor C3, an inductor L2 and a resistor R2. To increase coverage around the Smith Chart without adding more passive components, an optional quarter wavelength of cable 40 may be positioned between the generator 4 and the tuner 8b; this functions to shift an impedance 180° around the Smith Chart.

Figure 4:
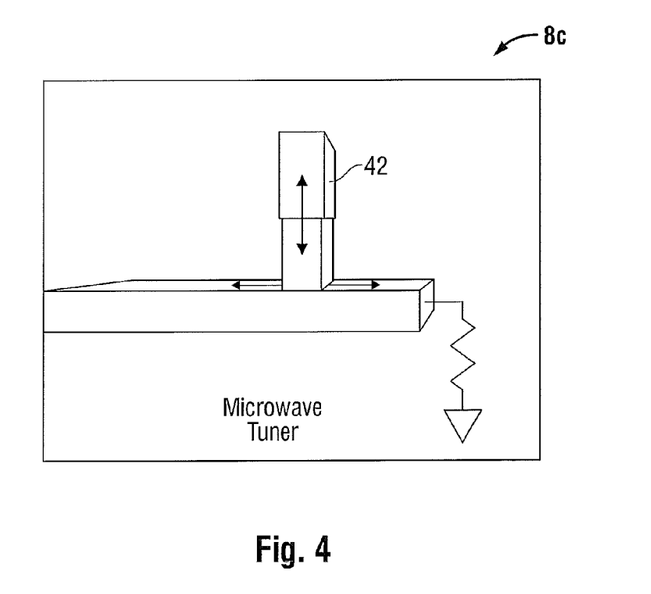
FIG. 4 is a schematic view of a microwave tuner configured for use with the system depicted in FIG. 1.

FIG. 4 illustrates a microwave tuner 8c. This type of tuner is suitable for testing the generator 4 when the generator 4 is configured to transmit electrosurgical energy in the microwave frequency range. In this particular embodiment, an adjustable tuning stub 42 that is connected to ground can be either an open or a short circuit node and may vary in length as dictated by controller 6. In certain embodiments, the tuning stub 42 can be moved towards or away from the load to shift the load around the Smith Chart. The location of the adjustable stub 42 shifts the load around the Smith Chart by placing the adjustable stub in parallel with the load. The microwave tuner 8b is relatively small when compared to the aforementioned tuners (or tuners yet to be described).

Figure 5:
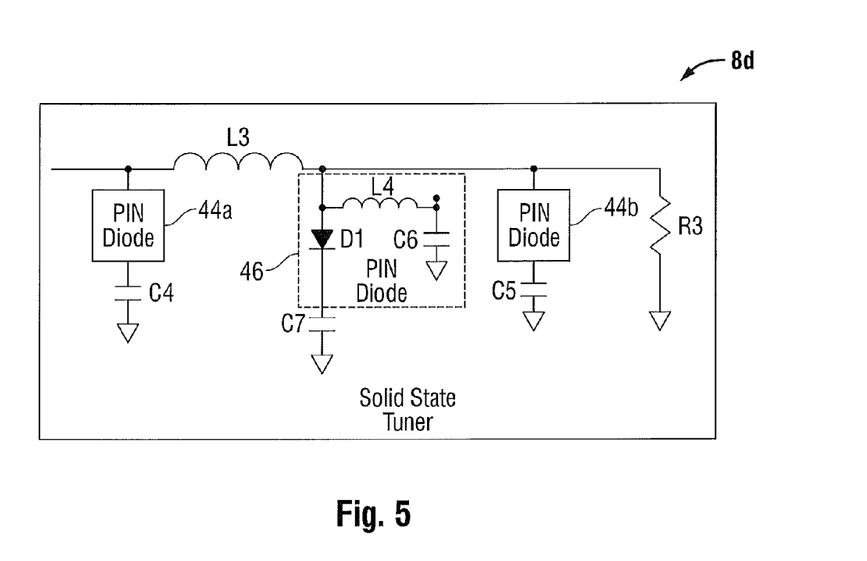
FIG. 5 is a schematic view of a solid state tuner configured for use with the system depicted in FIG. 1.

FIG. 5 illustrates a solid state tuner 8d. Solid state tuner 8d uses one or more pin diodes (two pin diodes 44a-44b illustrated) to "switch-in" respective tuning capacitors C4, C5 (which are connected to ground) and various taps on an inductor L3. Solid state tuner 8d includes a resistor R3 that is connected to ground. In the embodiment illustrated in FIG. 5, a bias line 46 is utilized to turn on and off the diodes 44a-44b and is isolated from the RF frequencies by a choke inductor L4 and a bypass capacitor C6. The bias line 46 includes a diode D1 in series with a capacitor C7 that is connected to ground. An advantage of the tuner 8d is that is has no mechanical parts and can have higher repeatability and reliability when compared to other tuners, e.g., tuner 8a.

Figure 6:
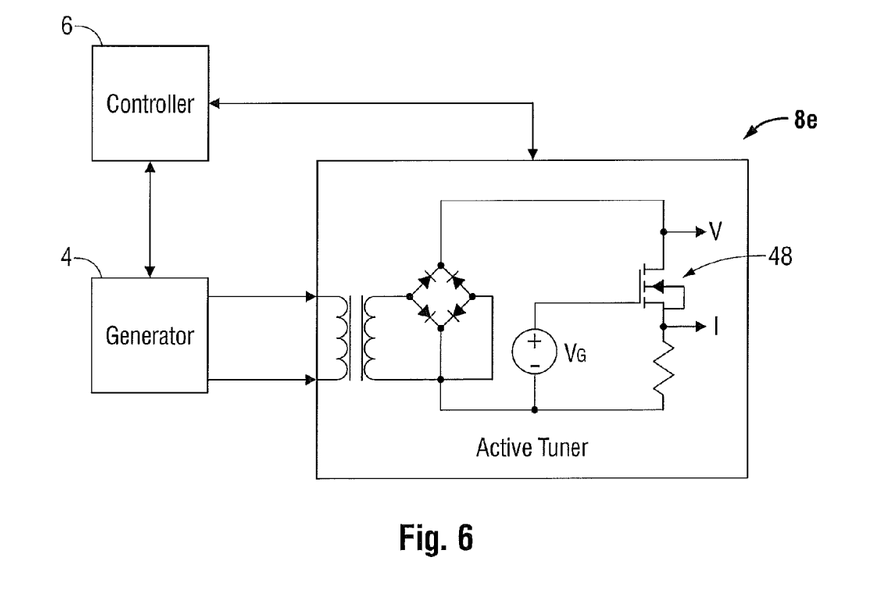
FIG. 6 is a schematic view of an active tuner configured for use with the system depicted in FIG. 1.

FIG. 6 illustrates an active tuner 8e that utilizes a FET 48 (or other suitable device) to increase or decrease a load of the active tuner 8e. In this instance, the controller 6 can adjust a gate voltage Vg, which adjusts an on resistance of the FET 48 which, in turn, increases and/or decreases the overall resistance of the active tuner 8e. Active tuner 8e includes a very fast response time and, in some instances, may be able to simulate an arcing event. An advantage of the tuner 8e when compared to the aforementioned tuners is that tuner 8e does not require mapping to a Smith Chart, i.e., the load of the tuner 8e is monitored using voltage and current.

Figure 7:
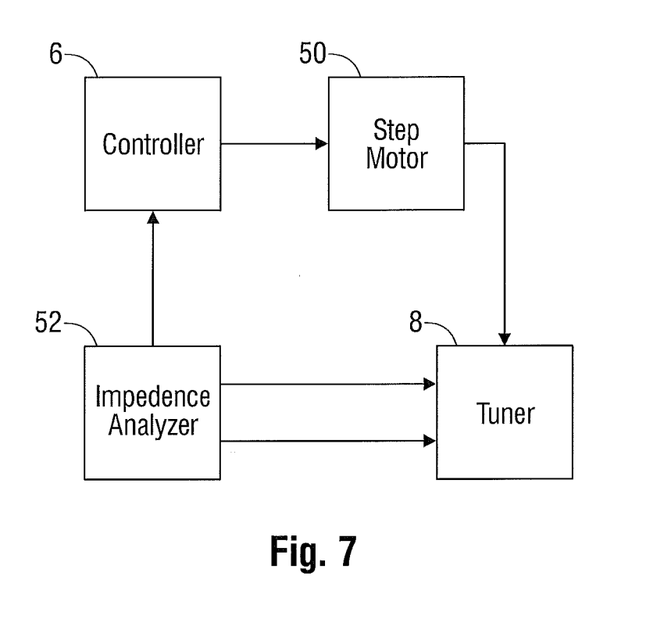
FIG. 7 is schematic block diagram of a sub-system of the system depicted in FIG. 1 utilized for mapping one of the tuners depicted with the system depicted in FIGS. 2-6.

With reference to FIG. 7, a step motor 50 is configured to operably couple to the controller 6 and one or more of the tuners 8 (for illustrative purposes, step motor 50 is described in terms of use with the passive tuner 8a) to control the tuner 8a to a specific impedance. Positions of the step motor 50 are utilized to vary one or more of the passive components in the tuner 8a and are then mapped to a corresponding value on the Smith Chart. In particular, step motor 50 is configured to couple to the tuner 8a to vary one or more of the first and second capacitors C1-C2, inductors L1 and/or resistor R1. The positions of the step motor 50 are then mapped to a corresponding value on the Smith Chart to control the tuner 8a to a specific impedance. To accomplish this, controller 6 is utilized to control the step motor 50 as the step motor 50 moves through each of the positions of the step motor 50 and measures an impedance value, e.g., complex impedance, of the load of the tuner 8a.

With continued reference to FIG. 7, an impedance analyzer 52 is configured to operably couple to the controller 6 and one or more of the tuners 8, e.g., tuner 8a. The impedance analyzer 52 is configured to measure the complex impedance of the load of the tuner 8a as the step motor 50 varies the complex impedance of the load. The measured complex impedances of the load and motor positions of the step motor 50 are stored in memory 32 of the controller 6.

Controller 6 is configured to operably couple to the generator 4 for retrieving the recorded data pertaining to the characteristic(s) of tissue, e.g., calculated tissue impedances that were previously mapped to the Smith Chart. Controller 6 is configured to compare the recorded data pertaining to the characteristic(s) of tissue with stored data pertaining to the plurality of impedance values that were previously obtained with the use of one of the tuners 8, e.g., tuner 8a and based on this comparison, the controller 6 adjusts a load of the tuner 8 to one or more of the plurality of impedance values. In particular, in a diagnostic testing or simulation sequence, the tuner 8 functions as a load "L" for an output of the generator 4 and an impedance of the load "L" of the tuner 8 may be varied by varying one or more of the passive components of the tuner 8.

Operation of the system 2 is described in terms of testing generator 4 for possible instabilities that may be associated with the generator 4 after and/or prior to use thereof.

For purposes herein, it is assumed that calculated impedance values have been previously obtained during an electrosurgical procedure, mapped to a Smith Chart and stored into memory 26 of generator 4.

Generator 4 may be coupled to the controller 6 and one or more of the aforementioned tuners 8, e.g., passive tuner 8a. Controller 6 downloads the calculated impedance values from the generator 4. In the illustrated embodiment, generator 4 was utilized to obtain the calculated impedances. Alternately, the external measurement device 3 may have been used to collect, record, calculate and, subsequently, store the impedance values into memory 26 of the generator 4. Controller 6 compares the calculated impedance values with known impedance values including corresponding step positions of the step motor 50 stored in memory 32.

With generator 4 coupled to the tuner 8a, generator 4 is activated to run through a simulated tissue sealing phase. Controller 6 activates the step motor 50 to move the step motor 50 to vary the inductance of the inductor L1 and/or capacitance of the first and second capacitors C1-C2 to vary the complex impedance of the tuner 8a. Varying the complex impedance of the tuner 8a around the Smith Chart "mimics" actual tissue response. The controller 6 can move through as many positions of the step motor 50 as needed to check for possible instabilities that may be associated with the generator 4.

As can be appreciated, the aforementioned system 2 overcomes the aforementioned drawbacks typically associated with conventional methods that are utilized to test electrosurgical generators. That is, system 2 tests the generator 4 through a tissue simulation that utilizes both real and imaginary parts of impedance and not just the real part as is utilized by conventional testing methods.

From the foregoing and with reference to the various figure drawings, those skilled in the art will appreciate that certain modifications can also be made to the present disclosure without departing from the scope of the same. For example, the system 2 may be utilized to support verification and validation of a specific design of a generator. Or, in certain instances, the system 2 may be utilized for realizing efficiency gains. Those skilled in the art will realize that the system 2 may be utilized to provide a host of other benefits not described herein.

While the Smith Chart has been described herein as representing impedances, the Smith Chart may be used to represent other parameters including, but not limited to, admittances, reflection coefficients, scattering parameters, noise figure circles, constant gain contours and regions for unconditional stability.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system, comprising:
an external measurement device configured to measure, collect and record data pertaining to at least one characteristic of tissue as the tissue is being electrosurgically treated;
a tuner, including at least one tuning circuit, configured to couple to an active and a return terminal of an RF output stage of an electrosurgical generator to complete a circuit with the RF output stage, the tuner is further configured to simulate a tissue load having a variable complex impedance for the electrosurgical generator when the electrosurgical generator is coupled to the tuner; and
a controller configured to couple to the electrosurgical generator for diagnostic testing thereof, the controller including stored data pertaining to a plurality of impedance values, the controller in operable communication with the external measurement device for retrieving the recorded data pertaining to the at least one characteristic of tissue and in operable communication with the tuner for varying a complex impedance of the load, the controller configured to compare the recorded data pertaining to the at least one characteristic of tissue with the stored data pertaining to the plurality of impedance values and to adjust the tuner to at least one of the plurality of impedance values during diagnostic testing of the electrosurgical generator.

2. A system according to claim 1, wherein a step motor is configured to operably couple to the controller and tuner, the controller configured to activate the step motor for varying the complex impedance of the load.

3. A system according to claim 2, further comprising an impedance analyzer configured to operably couple to the controller and tuner when the controller and tuner are not coupled to the electrosurgical generator or the external measurement device, the impedance analyzer configured to measure the complex impedance of the load as the step motor varies the complex impedance of the load, wherein the measured complex impedances of the load are stored in the controller as the data pertaining to the plurality of impedance values.

4. A system according to claim 1, wherein the tuner is selected from the group consisting of a passive tuner, a high frequency tuner, a microwave tuner, a solid state tuner and an active tuner.

5. A system according to claim 1, wherein the tuner is a passive tuner including a variable Pi network having a first variable capacitor connected in parallel with at least one variable inductor that is connected in parallel with a second variable capacitor that is connected in parallel with at least one resistor.

6. A system according to claim 5, wherein each of the first and second variable capacitors include a variable capacitance from 40 pF to 2,000 pF and the at least one inductor includes a variable inductance from 50 μH to 200 μH.

7. A system according to claim 1, further comprising a memory storing at least one Smith Chart including impedance data of the tissue based on the at least one characteristic of tissue measured by the external measurement device.

8. A method for testing electrosurgical generators, comprising:
providing an external measurement device configured to measure, collect and record data pertaining to at least one characteristic of tissue as the tissue is being electrosurgically treated;
coupling a tuner to an active and a return terminal of an RF output stage of an electrosurgical generator to complete a circuit with the RF output stage, the tuner including at least one tuning circuit configured to simulate a tissue load having a variable complex impedance for the electrosurgical generator when the electrosurgical generator is coupled to the tuner;
coupling the external measurement device to a controller for retrieving the recorded data pertaining to the at least one characteristic of tissue;
coupling the controller to the electrosurgical generator to perform a diagnostic test thereof, the controller including stored data pertaining to a plurality of impedance values;
coupling the controller to the tuner for varying a complex impedance of the load;
comparing the recorded data pertaining to the at least one characteristic of tissue with the stored data pertaining to the plurality of impedance values; and
adjusting the tuner to at least one of the plurality of impedance values during diagnostic testing of the electrosurgical generator.

9. A method according to claim 8, wherein providing the external measurement device includes providing the external measurement device as a component of the electrosurgical generator.

10. A method according to claim 8, including providing a step motor configured to operably couple to the controller and tuner.

11. A method according to claim 10, including activating the step motor for varying the complex impedance of the load.

12. A method according to claim 11, further providing an impedance analyzer configured to operably couple to the controller and tuner when the controller and tuner are not coupled to the electrosurgical generator or the external measurement device.

13. A method according to claim 12, including measuring the complex impedance of the load with the impedance analyzer as the step motor varies the complex impedance of the load.

14. A method according to claim 13, including storing the measured complex impedances of the load in the controller as the data pertaining to the plurality of impedance values.

15. A method according to claim 13, including storing step positions of the step motor in the controller, the step positions corresponding to the measured complex impedances of the load.

16. A method according to claim 8, wherein coupling the electrosurgical generator to the tuner includes selecting the tuner from the group consisting of a passive tuner, a high frequency tuner, a microwave tuner, a solid state tuner and an active tuner.

17. A method according to claim 16, wherein the tuner is a passive tuner including a variable Pi network having a first variable capacitor connected in parallel with at least one variable inductor that is connected in parallel with a second variable capacitor that is connected in parallel with at least one resistor.

18. A method according to claim 17, wherein each of the first and second variable capacitors include a variable capacitance from 40 pF to 2,000 pF and the at least one inductor includes a variable inductance from 50 μH to 200 μH.

19. A system for testing electrosurgical generators, comprising:
an electrosurgical generator configured to provide electrosurgical energy for electrosurgically treating tissue and to measure, collect and record data pertaining to at least one characteristic of tissue as the tissue is being electrosurgically treated;

a tuner configured to couple to an active and a return terminal of an RF output stage of the electrosurgical generator to complete a circuit with the RF output stage, the tuner including at least one tuning circuit including a load including at least three reactive components and at least one resistor, the tuning circuit configured to simulate a tissue load having a variable complex impedance for the electrosurgical generator when the electrosurgical generator is coupled to the tuner; and a controller including stored data pertaining to a plurality of impedance values, the controller configured to couple to the electrosurgical generator for diagnostic testing thereof and for retrieving the recorded data pertaining to the at least one characteristic of tissue, the controller configured to couple to a step motor that is configured to couple to the tuner for varying at least one of the at least three reactive components to vary a complex impedance of the load of the tuner, the controller configured to compare the recorded data pertaining to the at least one characteristic of tissue with the stored data pertaining to the plurality of impedance values and to adjust the tuner to at least one of the plurality of impedance values.

20. A system according to claim 19, further comprising an impedance analyzer configured to operably couple to the controller and tuner when the controller and tuner are not coupled to the electrosurgical generator, the impedance analyzer configured to measure the complex impedance of the load as the step motor varies the complex impedance of the load, wherein the measured complex impedances of the load are stored in the controller as the data pertaining to the plurality of impedance values.

21. A system according to claim 19, wherein the at least three reactive components includes a first variable capacitor connected in parallel with at least one variable inductor that is connected in parallel with a second variable capacitor that is connected in parallel with at least one resistor, wherein each of the first and second variable capacitors include a variable capacitance from 40 pF to 2,000 pF and the at least one variable inductor includes a variable inductance from 50 μH to 200 μH.

* * * * *